United States Patent [19]

Michaelson et al.

[11] 4,393,253

[45] * Jul. 12, 1983

[54] HYDROXYLATION OF OLEFINS

[75] Inventors: Robert C. Michaelson, Waldwick; Richard G. Austin, Ridgewood, both of N.J.

[73] Assignee: Exxon Research & Engineering Co., Florham Park, N.J.

[ * ] Notice: The portion of the term of this patent subsequent to Feb. 2, 1999, has been disclaimed.

[21] Appl. No.: 310,099

[22] Filed: Oct. 9, 1981

Related U.S. Application Data

[63] Continuation-in-part of Ser. No. 209,789, Nov. 24, 1980, Pat. No. 4,314,088.

[51] Int. Cl.$^3$ .................... C07C 29/03; C07C 33/20; C07D 307/77; C07C 59/105
[52] U.S. Cl. .................... 568/860; 260/398; 549/240; 568/811; 568/832; 568/833
[58] Field of Search ............... 568/860, 811, 832, 833; 260/398; 549/240

[56] References Cited

U.S. PATENT DOCUMENTS 4,314,088 2/1982 Austin et al. ............ 568/860

FOREIGN PATENT DOCUMENTS 54-145604 11/1979 Japan .

Primary Examiner—Joseph E. Evans
Attorney, Agent, or Firm—Robert A. Maggio

[57] ABSTRACT

A method for preparing polyols such as diols by catalytic hydroxylation of an olefinic compound by reacting the olefinic compound with an organic hydroperoxide and water in the presence of a catalyst comprising osmium compound and a specific halide co-catalyst is disclosed.

10 Claims, No Drawings

HYDROXYLATION OF OLEFINS

CROSS REFERENCE TO RELATED APPLICATION

The present application is a continuation-in-part of U.S. Patent Application Ser. No. 209,789, filed Nov. 24, 1980, issued as U.S. Pat. No. 4,314,088 the disclosure of which is herein incorporated by reference.

BACKGROUND OF THE INVENTION

1. Field of the Invention

This invention relates to the hydroxylation of olefins. In particular, it relates to a procedure for reacting an olefin, e.g. ethylene and propylene, with an organic hydroperoxide oxidant in the presence of a specific catalyst composition to produce the corresponding glycol.

2. Description of the Prior Art

It is well known from the technical literature, including patents, that olefins can be effectively oxidized with osmium oxide compounds, particularly osmium tetroxide, to their corresponding diols when the reaction is carried out with catalytic amounts of osmium tetroxide and a stoichiometric amount of a strong co-oxidizing agent.

More specifically, Japanese patent application No. Sho 54-145604, published Nov. 14, 1979, is directed to a process for hydroxylating olefins in the presence of $OsO_4$, a quaternary ammonium salt co-catalyst such as tetra ethyl ammonium bromide, and a peroxide including organo peroxides and $H_2O_2$ as the oxident. Selectivities to glycol of from about 4.5 to about 66% are disclosed. It is to be noted, however, that the critical component of the co-catalyst as implied in this patent is the quaternary ammonium cation rather than the particular identity of the anion, since the anion can be any of halogen, hydroxy, nitrate, perchlorate, sulfate, methane sulfonate, trifluoromethane sulfonate, and tetra fluoro borate ions, while the cation must always be quaternary ammonium. In contrast, the present invention recognizes that it is the identity of the anion which is critical, the critical anion being a halogen.

U.S. Pat. No. 2,414,385 discloses the use of hydrogen peroxide and a catalytically active oxide, such as osmium tetroxide, dissolved in an essentially anhydrous, non-alkaline, inert, preferably organic, solvent, to convert, by oxidation, unsaturated organic compounds to useful oxygenated products such as glycols, phenols, aldehydes, ketones, quinones and organic acids. The formation of glycols is achieved by conducting the reaction at temperatures of between several degrees below 0° C. and 21° C. Such low reaction temperatures drastically, and disadvantageously, reduce the reaction rate to commercially unacceptable levels. At temperatures greater than 21° C., the formation of aldehydes, ketones and acids is favored.

U.S. Pat. No. 2,773,101 discloses a method for recovering an osmium containing catalyst such as osmium tetroxide, by converting it to the non-volatile osmium dioxide form, distilling the hydroxylation product, reoxidizing the osmium dioxide to the volatile osmium tetroxide, and then recovering the same by distillation. Suitable oxidizing agents used to oxidize olefins, and re-oxidize the osmium dioxide, include inorganic peroxides such as hydrogen peroxide, sodium peroxide, barium peroxide; organic peroxides, such as t-butyl peroxide or hydroperoxide, benzoyl peroxide; as well as other well known oxidizing agents such as oxygen, perchlorates, nitric acid, and chlorine water. As with other methods of the prior art, the above process yields undesirable by-products (see col. 1 line 55) thus reducing the selectivity of the process.

U.S. Pat. No. 4,049,724 describes the preparation of glycols from alkenes and from unsaturated alcohols in an aqueous system using osmium tetroxide and specifying stable and water-soluble aliphatic hydroperoxides, such as tert-butyl hydroperoxide, while a critical pH of 8 to 12 is maintained by a suitable combination of alkali metal buffering compounds. The preparation of propylene glycol utilizing tert-butyl hydroperoxide is exemplified in the patent at a selectivity based on the hydroperoxide of 45 percent.

See also, K. B. Sharpless in JACS, Mar. 31, 1976, pp. 1986–7 which discloses that whereas alkaline solutions of hydrogen peroxide decomposed violently in presence of $OsO_4$, solutions of t-butyl hydroperoxide in the presence of base (tetraethylammonium hydroxide gave yields superior to that obtained with sodium or potassium hydroxide) and $OsO_4$ were stable and provided good yields of vicinal diols from a variety of olefins.

Recently, U.S. Pat. No. 4,203,926 discloses the heterogeneous catalysis of ethylene and propylene to the corresponding glycol in a process in which ethylbenzene hydroperoxide is reacted with the olefin in a two-phase liquid (organic-aqueous) reaction system in the presence of osmium tetroxide and cesium, rubidium or potassium hydroxide. This two-phase system requires organic soluble hydroperoxides and appears specific for ethylbenzene hydroperoxide.

None of the above references disclose the halogen ion containing co-catalysts of the present invention.

SUMMARY OF THE INVENTION

In one aspect of the present invention there is provided a process for hydroxylating olefins which comprises reacting at least one olefinic compound having at least one ethylenic unsaturation with water and at least one organic hydroperoxide in the presence of a catalyst composition under conditions and in a manner sufficient to convert at least one of said ethylenic unsaturation to its corresponding diol said catalyst composition comprising: (a) osmium tetroxide; and (b) at least one co-catalyst selected from the group consisting of alkali metal halide, alkaline earth metal halide, hydrogen halide, quaternary hydrocarbyl phosphonium halide, halogen, and transition metal halide said transition metal being selected from the group consisting of Fe, Co, Ni, Cu, V, Cr, Mn, Sc, Ti, Mo, Ru, Rh, Pd and W.

DETAILED DESCRIPTION OF THE INVENTION

The present invention is conducted by reacting at least one olefin with water and at least one organic hydroperoxide in the presence of a specifically defined catalyst composition under conditions and in a manner sufficient to hydroxylate said olefin.

1. Olefinic Compound

The olefinic compound which can be hydroxylated in accordance with this invention possesses at least one ethylenic unsaturation and typically has from 2 to 20 carbon atoms, including mono-olefinic compounds, diolefinic or polyolefinic compounds, both conjugated and nonconjugated, substituted, (e.g., with $C_6$ to $C_{14}$ aryl, and $C_1$ to $C_{10}$ alkyl) and unsubstituted aliphatic and alicyclic olefins, hydroxy-substituted olefinic compounds, olefinically unsaturated aliphatic carboxylic acids and anhydrides, such as oleic acid, 1,2,3,6-tetrahydrophthalic anhydride and the like. Illustrative olefins include ethylene, propylene, butylene, pentenes, normal hexenes, the octenes, cyclohexene, butadiene, styrene, vinyl cyclohexene, and the like. The preferred olefinic compounds for this process are the $C_2$ to $C_4$ lower olefins, i.e. ethylene, propylene and butylene or allyl alcohol. Mixtures of any of the above noted olefinic compounds can also be employed.

2. Catalyst Composition

(a) Osmium Tetroxide

The catalyst, osmium tetroxide, is used in catalytic quantities, i.e. effective to convert at least one ethylenic unsaturation to its corresponding diol. It has been found that from 0.01 to 10 millimols (mmols) of the catalyst per 100 ml of the total reaction mixture is suitable; however, it is preferred to carry out the reaction from about 0.03 to about 0.1 mmol of catalyst per 100 ml of the reaction mixture. The amount of catalyst can also be related to the amount of osmium metal that is used. Thus, about 5 to about 1,000 ppm, preferably about 25 to about 800 ppm osmium can be used, based on the total liquid contents of the reaction vessel. The order of addition of catalyst is not critical to obtain high selectivities to glycols, since osmium does not catalyze the decomposition of the hydrperoxide in the olefin's absence.

Osmium tetroxide is readily soluble in an organic polar solvent and can be dissolved in a said solvent for addition to the reactor.

Included within the term osmium tetroxide as used herein are osmium compounds which are or can be converted to osmium tetroxide during the course of reaction such as salts thereof including K, Na, and Li, osmates as well as other osmium oxides such as $OsO_2$, $OsO_3$, and the like.

(b) Co-Catalyst

The co-catalyst which is employed in conjunction with $OsO_4$ contains halogen. The co-catalyst increases the rate and/or selectivity of the hydroxylation reaction and provides for the regeneration of the catalytic state of osmium. The co-catalyst is defined herein to be selected from the group consisting of alkali metal (e.g. Li, Na, K, Rb, Cs, and Fr) and alkaline earth metal (e.g., Be, Mg, Ca, Sr, Ba, Ra) halides, hydrogen halides, quaternary hydrocarbyl phosphonium halides, halogens, and transition metal halides and mixtures of any of the above classes of co-catalysts as well as mixtures of any co-catalysts within each class.

More specifically, representative examples of alkali and alkaline earth metal halide co-catalysts (referred to herein as Group 1 co-catalysts) include lithium bromide, sodium bromide, potassium chloride, sodium iodide, potassium iodide, cesium chloride, magnesium chloride, calcium bromide, and barium fluoride and mixtures thereof.

The preferred Group I co-catalysts include sodium iodide, potassium iodide, and sodium bromide.

Representative examples of suitable hydrogen halides (referred to herein as Group 2 co-catalysts) include hydrogen: iodide, chloride, fluoride, and bromide and mixtures thereof, preferably hydrogen iodide, and hydrogen bromide.

Representative examples of suitable quaternary hydrocarbyl phosphonium halides (referred to herein as Group 3 co-catalysts) include those represented by the structural formula:

$$(R)_4P^+X^- \qquad (I)$$

wherein each R is a hydrocarbyl group independently selected from the group consisting of substituted and unsubstituted: alkyl, typically alkyl having from about 1 to about 30 carbons, preferably from about 1 to about 20 carbons, and most preferably from about 1 to about 10 (e.g. 1-5) carbons, aryl, preferably aryl having from 6 to about 14 carbons, and most preferably from 6 to about 10 carbons, aralkyl, and alkaryl, typically aralkyl and alkaryl wherein the alkyl and aryl portions thereof are as defined immediately above respectively; said R substituents including hydroxyl; halide; ether groups, typically ether groups represented by the structural formulae: $-O-R_1$, $-R_1-O-R_2$, wherein $R_1$ and $R_2$ are independently selected from the group consisting of alkyl, typically about $C_1$ to about $C_{10}$ alkyl, preferably about $C_1$ to about $C_5$ alkyl, and most preferably about $C_1$ to about $C_3$ alkyl; and ester groups, typically ester groups represented by the structural formulae:

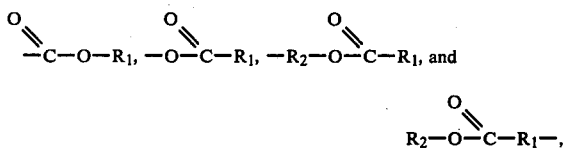

wherein $R_1$ and $R_2$ are as defined above; and wherein X in structural formula 1 is halide, i.e. F, Cl, Br, and I. Preferably R is tetralkyl or tetra aryl as defined above.

Representative examples of Group 3 co-catalysts include tetramethyl phosphonium bromide, tetrapropyl phosphonium fluoride, tetraethyl phosphonium chloride, tetradecyl phosphonium iodide, tetraphenyl phosphonium chloride, dimethyl diethyl phosphonium bromide, methytriethyl phosphonium chloride, tetrabutyl phosphonium iodide, phenyltrimethyl phosphonium chloride, diphenyl diethyl phosphonium bromide, tetra 2-(methoxy)ethyl phosphonium chloride, tetra 4-(propoxy methyl)phenyl phosphonium bromide, di 3-(methoxy carbonyl)propyl-diethyl phosphonium iodide, di 4-(ethyl carbonyloxy)butyl-dimethyl phosphonium chloride, tetra 5-(ethoxy carbonyl methyl)pentyl phosphonium bromide, tetra 4-hydroxy butyl phosphonium chloride, tetra 3-chloro propyl phosphonium bromide, and mixtures thereof.

Preferred Group 3 co-catalysts include: tetra alkyl and tetra aryl phosphonium halides such as tetra ethyl phosphonium chloride, and bromide.

Representative examples of halogen co-catalysts (referred to herein as Group 4 co-catalysts) include $F_2$, $Cl_2$, $Br_2$, and $I_2$, preferably $I_2$.

Transition metal halides (referred to herein as Group 5 co-catalysts) typically are salts having a cation of a transition metal and a halide anion.

Representative examples of such transition metals include those with a variable oxidation state such as Fe, Co, Ni, Cu, V, Cr, Mn, Sc, Ti, Mo, Ru, Rh, Pd, and W.

The preferred transition metals include Cu, Fe, Ni, Co, and Mn.

Representative examples of Group 5 co-catalysts include $FeF_3$, $FeCl_3$, $FeBr_3$, $FeF_2$, $FeCl_2$, $FeBr_2$, $FeI_2$, $CoCl_2$, $CoF_3$, $CoF_2$, $NiF_2$, $NiBr_2$, $NiI_2$, $NiCl_2$, $CuF_2$, $CuBr_2$, $CuI_2$, $CuF_2$, $CuI$, $CuCl$, $CuBr$, $VF_5$, $VF_4$, $VF_3$, $VF_2$, $VCl_4$, $VCl_3$, $VBr_4$, $VBr_3$, $VI_3$, $CrF_2$, $CrF_3$, $CrF_4$, $CrF_5$, $CrF_6$, $CrCl_3$, $CrCl_4$, $CrBr_3$, $CrBr_4$, $CrI_3$, $MnCl_2$, $MnCl_3$, $MnCl_4$, $MnBr_3$, $MnI_3$, $ScCl_3$, $ScBr_3$, $ScFl_3$, $TiCl_4$, $TiBr_4$, $TiFl_4$, $MoCl_3$, $Mo_2Cl_{10}$, $MoBr_4$, $Mo_2F_9$, $MoF_6$, $MoF_5$, $RuF_5$, $RuF_3$, $RuF_4$, $RuF_6$, $RuCl_3$, $RuCl_4$, $RuCl_6$, $RuBr_6$, $RhF_3$, $RhF_4$, $RhF_6$, $PdF_2$, $PdCl_2$, $PdBr_2$, $PdI_2$, $WCl_6$, $WBr_5$, $WCl_3$, $WBr_3$, and $WI_3$.

Preferred Group 5 co-catalysts include $WCl_6$.

It is recommended for best results that the most preferred valence of the transition metals of Group 5 co-catalysts as initially employed be that which represents the highest stable oxidation state thereof. While this is not critical, it avoids the need in some instances to oxidize the transition metal in-situ so that it can be reduced.

The co-catalyst(s) is employed in amounts effective to increase the rate and/or selectivity of the hydroxylation reaction. Thus, while any effective amount of co-catalyst can be employed, such effective amounts typically will vary from about 5 to about 100,000 ppm., preferably from about 50 to about 10,000 ppm., and most preferably from about 100 to about 1000 ppm., by weight based on the total weight of the liquid contents of the reaction vessel.

Alternatively, the amount of co-catalysts can be expressed as a molar ratio between the molar amount of halide species in the co-catalyst to the molar amount of osmium metal in the $OsO_4$. Accordingly, such molar ratios typically will vary from about 2:1 to about 100:1, preferably from about 2:1 to about 50:1, and most preferably from about 2:1 to about 25:1.

(3) Inert Polar Solvents

While the hydroxylation reaction can be conducted in a heterogeneous system, the preferred mode for conducting the hydroxylation reaction is in a liquid reaction mixture, preferably provided as a homogeneous or substantially homogeneous medium and preferably but optionally by using an inert, preferably polar organic solvent to dissolve where possible the catalyst composition and reactants. The solvent is entirely optional, however, and when present functions primarily to achieve even dispersal of heat in the reaction mixture. Partial immiscibility of the solvent with water is acceptable although not preferred. By inert solvent is meant one which does not undergo oxidation during the course of the reaction.

Representative inert solvents include organic polar solvents which can be an aliphatic or aromatic alcohol having from one to about ten carbon atoms, an aliphatic or aromatic ketone having from three to about ten carbon atoms, an aliphatic or alicyclic ether having from two to about ten carbon atoms, a glycol having from two to about ten carbon atoms, a N,N-dialkyl amide having from three to about ten carbon atoms, an aliphatic or aromatic sulfoxide having from two to about fourteen carbon atoms and an aliphatic or aromatic sulfone having from two to about fourteen carbon atoms.

Examples of suitable polar solvents include methanol, ethanol, propanol, butanol, hexanol, decanol, t-butyl alcohol, benzyl alcohol, acetone, methylethyl ketone, methylbutyl ketone, acetophenole, ethylene glycol, propylene glycol, diethylene glycol, tetraethylene glycol, dimethyl formamide, diethyl formamide, dimethyl acetamide dimethyl sulfoxide, diethyl sulfoxide, di-n butyl sulfoxide, diphenyl sulfoxide, dibenzyl sulfoxide, dimethyl sulfone, diethyl sulfoxide, dibenzyl sulfoxide, diphenyl sulfone, acetonitrile, pyridine, dioxane, tetrahydrofuran, tetrahydropyran dioxolane, and the like, and mixtures thereof. Preferred solvents are those which are completely miscible with water such as is acetonitrile, dioxane, acetone, diethyl ether, primary alcohols such as methanol, ethanol, and isobutanol and tertiary alcohols such as tertiary butanol.

The most preferred solvent(s) is the hydroxylated olefin which possesses at least one glycol functionality or mixtures of the product glycol and the product alcohol derived from the organohydroperoxide.

For example, when ethylene is hydroxylated using t-butyl hydroperoxide, the most preferred solvent is ethylene glycol, t-butyl alcohol, or a mixture of ethylene glycol and t-butyl alcohol, the latter being formed in-situ from t-butyl hydroperoxide. The former (product glycol) avoids solvent separation process steps and the latter is economical since the ethylene glycol and t-butyl alcohol are both saleable products which have to be separated anyway. In either instance, an additional solvent separation step is avoided.

The inert solvent is preferably employed in amounts sufficient to achieve a homogeneous or substantially homogeneous solution with respect to at least the olefin and catalyst composition. Typically, such amounts can vary from about 0 to about 98 percent, preferably from about 30 to about 98 percent, and most preferably from about 50 to about 80 percent, by weight, based on the total weight of the reaction mixture.

(4) Organic Hydroperoxide

The oxidant for the hydroxylation reaction is at least one organic hydroperoxide conventionally employed for such reactions.

Conventional organohydroperoxides include those having the formula:

wherein R″ is a substituted or unsubstituted: alkyl, typically about $C_3$ to about $C_{20}$, preferbly about $C_3$ to about $C_{10}$, most preferably about $C_3$ to about $C_6$ alkyl; aryl, typically $C_6$ to $C_{14}$, preferably $C_6$ to $C_{10}$, most preferably $C_6$ aryl; aralkyl and alkaryl wherein the aryl and alkyl groups thereof are as defined immediately above; cycloalkyl, typically about $C_4$ to about $C_{20}$, preferably about $C_4$ to about $C_{10}$, most preferably about $C_4$ to about $C_8$ cycloalkyl; as well as oxacyclics having 1 to about 5 oxygens and preferably 3 to about 20 carbons, and azacyclics having 1 to about 5 nitrogens and preferably about 3 to about 20 carbons; and wherein the substituents of said R″ group include halogen, hydroxyl, ester and ether groups.

Representative examples of suitable organohydroperoxides include ethyl benzene hydroperoxide, t-butyl hydroperoxide, t-amyl hydroperoxide, cumene hydroperoxide, 2-methyl-2-hydroperoxy-methyl propionate, 2-methyl-2-hydroperoxy propanoic acid, pyrrolehydroperoxide, furan hydroperoxide, 2-butylhydroperoxide, cyclohexyl hydroperoxide, 1-phenylethyl hydroperoxide and mixtures thereof.

The most preferred organohydroperoxides include t-butyl hydroperoxide, ethyl benzyl hydroperoxide, and t-amyl hydroperoxide. Frequently these hydroperoxides are made by the molecular oxygen oxidation of the corresponding hydrocarbon which also produces an alcohol as a by-product. For example, when isobutane is oxidized with molecular oxygen there is produced tertiary butyl hydroperoxide and tertiary butyl alcohol. It is not necessary to separate the alcohol from the hydroperoxide since the alcohol can function as a diluent or solvent.

The amount of organohydroperoxide employed is not critical and can vary widely. Generally, the organohydroperoxide is employed in less than stoichiometric requirements (i.e., less than 1:1 molar ratio of organohydroperoxide per mole of ethylenic unsaturation in the olefin to be hydroxylated.) Thus, while any amount of hydroperoxide effective to hydroxylate the olefin can be employed, it is preferred that such effective amounts constitute a ratio of moles of ethylenic unsaturation in the olefin to moles of organohydroperoxide of from about 0.5:1 to about 100:1, preferably about 1:1 to about 20:1 and most preferably about 2:1 to about 10:1.

The organohydroperoxide is preferably employed as an aqueous solution comprising from about 25 to about 90%, preferably from about 30 to about 80%, and most preferably from about 30 to about 75%, by weight hydroperoxide, based on the weight of the aqueous hydroperoxide solution, although it can be added in anhydrous form.

(5) Water

It is believed that the hydroxylation of the olefin occurs according to the following reaction (using ethylene and t-butyl hydroperoxide as illustrative reactants):

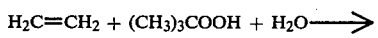

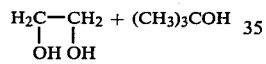

From this it is seen that the water is to be present in at least a stoichiometric amount based on the amount of olefin ethylenic unsaturation to be hydroxylated. The source of this water may vary. Water can be added separately, preferably as the solvent for the organohydroperoxide. Consequently, water is provided to, and/or is present, in the initial reaction mixture in at least a stoichiometric molar ratio with the molar amount of ethylenic unsaturation of the olefin to be hydroxylated. Such ratios preferably also are present in the reaction mixture at any given time after start-up. Accordingly, water is present in the reaction mixture at molar ratios of water to olefin ethylenic unsaturation to be hydroxylated in the reaction mixture of from about 1:1 to about 100:1 (e.g., 1:1 to 10:1), preferably from about 1:1 to about 50:1 (e.g., 1:1 to 5:1), and most preferably from about 1:1 to about 20:1 (e.g., 1.5:1). Such molar ratios typically can be achieved by controlling the amount of water in the reaction mixture to be from about 10 to about 90 percent, preferably from about 15 to about 85 percent, and most preferably from about 20 to about 60 percent, by weight, based on the total weight of the reaction mixture. Preferably the amount of water employed is less than that which will cause separation of the reaction mixture into an aqueous phase and organic phase although this is not a critical condition.

(6) Reaction Conditions

Since the preferred olefins to be hydroxylated, e.g., ethylene and propylene, are gases, the olefin is incorporated into the reaction system by pressuring the reactor with the olefin. Although the magnitude of the pressure is not critical, it determines the amount of the olefin that is present in the reaction liquid and therefore affects the rate of the reaction. It is believed that a pressure between about 5 and about 1,000 psig is useful for ethylene, and a pressure of between about 5 and about 1500 psig is useful for propylene. However, it is generally suitable to operate within the pressure ranges of typically between about 50 and 500 psig, preferably between about 50 and about 200 psig (e.g. 50 to 150 psig) for ethylene, and a pressure typically between about 10 and about 500 psig, preferably 50 and about 200 psig for propylene, to provide a suitable reaction rate without requiring high pressure equipment. The reaction is preferably carried out with olefin in excess of stoichiometry (i.e., greater than 2 moles of olefinic unsaturation to be hydroxylated per mole of hydroperoxide) to substantially completely react all of the hydroperoxide in the reaction mixture, and more preferably, at least about a 25% excess of stoichiometry of the olefin. It is advantageous to carry out reactions in the liquid phase; therefore, sufficient pressure is employed to maintain the reactants in the liquid phase, at least to the extent that some olefin is in the liquid phase. For liquid reactants, atmospheric pressure is suitable.

In practice, the osmium tetroxide or precursor thereof is readily charged into the reaction vessel as a solution in the polar solvent, e.g., t-butanol, along with the co-catalyst, inert polar solvent, hydroperoxide and water prior to pressuring the vessel with olefin. It is useful also to heat up the contents of the vessel prior to introduction of the olefin.

The hydroxylation reaction is carried out at a moderate temperature. At higher temperatures the reaction rate increases substantially but this can occur at a significant reduction in selectivity to the glycol. At very low temperatures, the selectivity to glycol is excellent but the reaction rate is slow. Within these constraints, it has been found that a moderate reaction temperature range of about 0° to 200° C. (e.g., 25° to 200° C.) is desirable, preferably from 0° to 100° C., and optimally from 25° to 100° C. (e.g., 25° to 50° C.).

The pH of the reaction mixture during the hydroxylation reaction while not critical preferably will not be allowed to drop below about 4, preferably not below 6. Likewise, the pH of the reaction preferably will not be allowed to exceed about 12, although the process can still be conducted at pH's as high as 14. Accordingly, the pH of the reaction mixture typically will be maintained between about 4 and 12, preferably between about 6 and about 12, and most preferably between about 7 and about 12. The pH of the reaction mixture can be controlled by any suitable means such as by the use of conventional buffers or base where desired.

The hydroxylation reaction can be carried out as a batch reaction, or as a continuous reaction. In the batch reaction, all the necessary components are placed in a reaction vessel and the reaction is allowed to proceed for about ½ to about 2 hours for substantially complete reaction of the hydroperoxide. The reaction can be carried out in a continuous manner by metering the reaction components into an agitated tank reactor, or a series of tank reactors, pressured with the olefin and removing the reaction product mixture at an appropriate rate to maintain the reactor liquid level.

The reaction product mixture including inerts and by-products (after the removal of unreacted gaseous olefin) includes the diols, e.g., ethylene or propylene glycol, the polar solvent, the alcohol decomposition residue of the hydroperoxide, an osmium compound, the co-catalyst and water but most important is preferably a single phase mixture. Recovery of the product, e.g., ethylene glycol, is easily accomplished by fractional distillation.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples unless otherwise specified selectivity, conversion and yield are calculated as follows:

$$\% \text{ selectivity} = \frac{\text{moles of glycol}}{\text{moles of oxygenated product}} \times 100$$

$$\% \text{ conversion} = \frac{\text{moles of product}}{\text{moles of hydroperoxide charged}} \times 100$$

$$\% \text{ yield} = \% \text{ conversion} \times \% \text{ selectivity}$$

Furthermore, all product analysis is conducted by gas chromatography.

EXAMPLE I

Into a 300 ml titanium autoclave is charged 0.023 g of osmium tetroxide as a 0.5 weight percent solution thereof in t-butanol, 0.500 g sodium bromide, 54.9 g methanol and 11.1 g of t-butyl hydroperoxide as a 70% by weight solution thereof in water designated herein as (70%/H$_2$O). The solution is warmed to 40° C. and then ethylene (200 psig) is added. After stirring for 20 minutes, the product solution is analyzed by gas chromatography and indicates the production of 2.72 g of ethylene glycol which is a 99% selectivity and 54.9% yield based on the tertiary butyl hydroperoxide charged.

EXAMPLE II

Into a 300 ml titanium autoclave is charged 0.050 g of osmium tetroxide (0.5%/t-butanol solution), 1.09 g sodium bromide, 46.0 g water, and 15.1 g of tertiary butyl hydroperoxide (70%/H$_2$O). To this solution is added 31.0 g of propylene and the reaction mixture is stirred at 25° C. for two hours. Propylene glycol (4.0 g) is produced in an amount which corresponds to a 86% selectivity and 48.0% yield.

EXAMPLE III

Into a 300 ml titanium autoclave is charged 0.026 g of osmium tetroxide (0.5%/t-butanol solution), 0.25 g sodium iodide, 66.6 g of methanol and 15.6 g of tertiary butyl hydroperoxide (70%/H$_2$O). The solution is warmed to 40° C. with stirring and ethylene (400 psig) is added. After stirring for thirty minutes, the reaction is cooled. Ethylene glycol (3.92 g) is produced in an amount indicating a selectivity of 99% and yield of 54.5%.

EXAMPLE IV

Into a 300 ml titanium autoclave is charged 0.04 g OsO$_4$, 7.2 g t-butyl hydroperoxide (70%/H$_2$O), 0.50 g sodium bromide, 42.6 g t-butanol, and 3.0 g water. The contents are warmed to 40° C. and propylene (32.0 g) is added. The reaction is stirred at this temperature for thirty minutes. Propylene glycol (2.80 g) is produced in an amount corresponding to a selectivity of 77% and a yield of 65.7%.

EXAMPLE V

A similar run to Example IV using sodium iodide in place of sodium bromide gave comparable yield of propylene glycol.

EXAMPLE VI

Into a 300 ml titanium autoclave is charged 5 g of a 0.4 weight % solution of OsO$_4$ in water (0.1 mmole OsO$_4$), 20 g t-butyl alcohol, 0.31 g WCl$_6$ and 5.0 g 1-octene. To the resulting reaction mixture under continuous stirring is added slowly 3.0 g of a solution of t-butyl hydroperoxide in water (70%/H$_2$O) over a period of 15 minutes. The temperature of the reaction mixture varies between 27° and 47° C. The reaction mixture is stirred for an additional 30 minutes at the aforedescribed temperature range. The selectivity to 1,2-octane diol is 44% and the conversion is 100%.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for hydroxylating olefins which comprises reacting at least one olefinic compound having at least one ethylenic unsaturation with water and at least one organic hydroperoxide in the presence of a catalyst composition under conditions and in a manner sufficient to convert at least one of said ethylenic unsaturation to its corresponding diol said catalyst composition comprising:
   (a) Osmium tetroxide; and
   (b) at least one co-catalyst selected from the group consisting of alkali metal halide, alkaline earth metal halide, hydrogen halide, quaternary hydrocarbyl phosphonium halide, halogen, and transition metal halide said transition metal being selected from the group consisting of Fe, Co, Ni, Cu, V, Cr, Mn, Sc, Ti, Mo, Ru, Rh, Pd and W.

2. The process of claim 1 wherein the transition metal is selected from the group consisting of Cu, Fe, Ni, Co, and Mn.

3. The process of claim 1 wherein the catalyst composition possesses a molar ratio of halide species in the co-catalyst to osmium metal in the OsO$_4$ of from about 2:1 to about 100:1.

4. The process of claim 1 wherein the quaternary hydrocarbyl phosphonium halide is represented by the structural formula

wherein each R is independently selected from the group consisting of substituted and unsubstituted alkyl, aryl, aralkyl and alkaryl, and X is selected from the group consisting of Cl, F, Br, and I.

5. The process of claim 1 wherein the co-catalyst is selected from the group consisting of sodium iodide, sodium bromide, potassium iodide, hydrogen iodide, hydrogen bromide, tetraethyl phosphonium chloride, tetra ethyl phosphonium bromide, tungsten hexachloride and mixtures thereof.

6. The process of claim 1 wherein the organic hydroperoxide is selected from the group consisting of t-butyl hydroperoxide, ethyl benzyl hydroperoxide, t-amyl hydroperoxide and cumene hydroperoxide.

7. The process of claim 1 wherein the olefinic compound is selected from the group consisting of ethylene, propylene and mixtures thereof.

8. A process for hydroxylating olefins which comprises admixing to form a liquid reaction mixture, at least one olefinic compound having at least one ethylenic unsaturation, at least one organic hydroperoxide, water in at least a stoichiometric molar ratio with the moles of ethylenic unsaturation to be hydroxylated, and a catalyst composition, under conditions and in a manner sufficient to convert at least one of said ethylenic unsaturation to its corresponding diol hydroxylation product, said catalyst composition comprising:
(a) osmium tetroxide; and
(b) at least one co-catalyst selected from the group consisting of alkali metal halide, alkaline earth metal halide, hydrogen halide, quaternary hydrocarbyl phosphonium halide, halogen, and transition metal halide said transition metal being selected from the group consisting of Fe, Co, Ni, Cu, V, Cr, Mn, Sc, Ti, Mo, Ru, Rh, Pd, and W.

9. The process of claim 8 wherein the liquid reaction mixture additionally comprises at least one inert organic solvent.

10. The process of claim 9 wherein the inert organic solvent is the hydroxylation product.

* * * * *